(12) United States Patent
Banerjee et al.

(10) Patent No.: US 8,343,471 B2
(45) Date of Patent: Jan. 1, 2013

(54) NANOPARTICULATE IN-SITU GELS OF TPGS, GELLAN AND PVA AS VITREOUS HUMOR SUBSTITUTES

(75) Inventors: Rinti Banerjee, Mumbai (IN); Edmund Carvalho, Mumbai (IN)

(73) Assignee: Indian Institute of Technology Bombay, Mumbai (IN)

( * ) Notice: Subject to any disclaimer, the term of this patent is extended or adjusted under 35 U.S.C. 154(b) by 12 days.

(21) Appl. No.: 13/140,747

(22) PCT Filed: Sep. 3, 2010

(86) PCT No.: PCT/IB2010/002180
§ 371 (c)(1),
(2), (4) Date: Jun. 17, 2011

(87) PCT Pub. No.: WO2011/135400
PCT Pub. Date: Nov. 3, 2011

(65) Prior Publication Data
US 2012/0082730 A1    Apr. 5, 2012

(30) Foreign Application Priority Data
Apr. 30, 2010 (IN) .................................. 1392/2010

(51) Int. Cl.
*A61K 31/74* (2006.01)
(52) U.S. Cl. .................................................... 424/78.04
(58) Field of Classification Search .................... None
See application file for complete search history.

(56) References Cited

U.S. PATENT DOCUMENTS
2006/0246145 A1  11/2006  Chang et al.
2006/0251581 A1  11/2006  McIntyre et al.
2009/0220572 A1  9/2009   Deschatelets et al.

FOREIGN PATENT DOCUMENTS
WO    WO-2006/039458    4/2006

OTHER PUBLICATIONS

Chirila, T.V. et al., "Synthetic Polymers as Materials for Artificial Vitreous Body: Review and Recent Advances," J. Biomater. Appl., Oct. 1994, vol. 9, No. 2, pp. 121-137.
Chirila, T.V. et al., "The use of Hydrophilic Polymers as Artificial Vitreous," Prog. Polym. Sci., 1998, vol. 23, pp. 475-508.
Colthurst, M. et al., "Biomaterials used in the posterior segment of the eye," Biomaterials, 2000, vol. 21, pp. 649-665.
De Campos, A.M. et al., "Chitosan Nanoparticles as New Ocular Drug Delivery Systems: in Vitro Stability, in Vivo Fate, and Cellular Toxicity," Pharmaceutical Research, May 2004, vol. 21, No. 5, pp. 803-810.
Delinger, J.L. et al., "Replacement of the Liquid Vitreus with Sodium Hyaluronate in Monkeys II. Long-term Evaluation," Exp. Eye Res., 1980, vol. 30, pp. 101-117.
Giordano, G. et al., "Silicone Oils as Vitreous Substitutes," Prog. Polym Sk., 1998, vol. 23, pp. 509-532.
International Search Report and Written Opinion for PCT/IB2010/002180 mailed Dec. 16, 2010.
Jain, D. et al., "Biodegradable hybrid polymeric membranes for ocular drug delivery," Acta. Biomater., 2010, vol. 6, No. 4, pp. 1370-1379.
Maruoka, S. et al., "Biocompatibility of Polyvinylalcohol Gel as a Vitreous Substitute," Current Eye Research, 2006, vol. 31, pp. 599-606.
Siddaramaiah, S. et al., "Studies on Biopolymers for Ophthalmic Drug Delivery," Journal of Macromolecular Science, 2007, vol. 44, No. 2, pp. 229-234.
Soman, N. et al., "Artificial vitreous replacements," Bio-Medical Materials and Engineering, 2003, vol. 13, No. 1, pp. 59-74.
Suri, S. et al., "Biophysical Evaluation of Vitreous Humor, Its Constituents and Substitutes," Trends Biomater. Artif. Organs, 2006, vol. 20, No. 1, pp. 72-77.
Suri, S. et al., "in Vitro Evaluation of in Situ Gels as Short Term Vitreous Substitutes," Journal of Biomedical Materials Research Part A., 2006, vol. 79A, No. 3, pp. 650-664.
Swindle, K. E. et al., "Rabbit study of an in situ forming hydrogel vitreous substitute," Invest. Ophthalmol. Vis. Sci., Oct. 2009, vol. 50, No. 10, pp. 4840-4846.
Swindle, K.E. et al., "in situ formation of hydrogels as vitreous substitutes: Viscoelastic comparison to porcine vitreous," J. Biomed. Mater. Res. A., 2008, vol. 87, No. 3, pp. 656-665.
Swindle, K.E. et al., "Recent advances in polymeric vitreous substitutes," Expert Rev. Ophthalmol., 2007, vol. 2, No. 2, pp. 255-265.

*Primary Examiner* — Carlos Azpuru
(74) *Attorney, Agent, or Firm* — Foley & Lardner LLP

(57) ABSTRACT

The present technology provides a nanoparticulate in-situ gelling vitreous substitute, which is a liquid at room temperature to aid easy administration, such as e.g. through a small needle incision, and forms a gel within the eye, which is hydrophilic in nature, similar to the natural vitreous. The vitreous substitute formulation may include a water-soluble natural or synthetic polymer and a gelling-agent which are blended together in the presence of a cross linker, to form a gel having the properties of the vitreous humor. The process of cross linking and gelation may occur in-situ. This can be achieved by dispensing to the eye, different components of the vitreous substitute in liquid state, along with the cross linking agent.

20 Claims, 12 Drawing Sheets

Y axis: nmoles of malondialdehyde/mole lipid

NANOPARTICULATE IN-SITU GELS OF TPGS, GELLAN AND PVA AS VITREOUS HUMOR SUBSTITUTES

CROSS-REFERENCE TO RELATED APPLICATIONS

This application is the U.S. National Stage of Patent Cooperation Treaty Application No. PCT/IB2010/002180, filed Sep. 3, 2010, which claims priority to Indian Patent Application No. 1392/MUM/2010, filed Apr. 30, 2010, both of which are hereby incorporated by reference in their entirety.

TECHNICAL FIELD

The present technology relates generally to vitreous substitutes for use in ocular therapy and treatment of vitroretinal diseases. In particular, the present technology relates to the field of biodegradable nanoparticulate vitreous substitutes capable of gelling in-situ and delivering ocular drugs and actives.

BACKGROUND

The following description is provided to assist the understanding of the reader. None of the information provided or references cited is admitted to be prior art to the present technology.

The vitreous humor is an approximately spherical transparent gel and has a weight of approximately 4 g and a volume of about 4 mL, occupying a substantial volume in the eye. It has a significant content of water, about 98%. The vitreous does not adhere to the retina, except at three places: all around the anterior border of the retina, at the macula, and at the optic nerve disc. The vitreous is hydrophilic in nature with a water contact angle of 25-27. Light transmitted by the vitreous humor is in the range of 85-95% between the wavelengths 400-700 nm allowing maximum light to reach the retina resulting in clear vision. Some of the ailments that cause posterior segment disorders are spontaneous-retinal detachment, degeneration, age related macular disorder (ARMD), diabetic retinopathy, trauma-accidental or surgical, infection-toxocara/syphilis, tumors. Infectious conditions may respond to drug therapy, while tumors usually require surgery and may involve the loss of the eye. However, in many of these conditions, the direct cause of blindness is either neovascularization or retinal detachment. The various forms of retinal detachment are rhegmatogenous retinal detachment, tractional contractile membranes formed upon the retina, leading to the neural retina being pulled off the retinal pigment epithelium: exudative, where a build-up of fluid in the subretinal space beneath the neural retina is caused by disruption of the choroid leads to the elevation and detachment of the retina from the retinal pigment epithelium. In the case of ARMD, there is neovascularization which is subretinal, while in diabetic retinopathy, the neovascularization is intravitreal leading to vitreous hemorrhage. The treatments available for these pathologies are limited.

Vitreoretinal diseases are a major cause of blindness worldwide. These include retinal detachment, diabetic retinopathy and age related degeneration of the vitreous. Other disorders that cause retinal detachment include severe ocular infections, inflammations, and traumatic injuries to the eye. Age-related macular degeneration and macular holes are also conditions that require retinal support materials and drug therapy. All of these conditions require the damaged vitreous humor to be removed and replaced either partially or totally by artificial substitutes. Vitreous replacement is also required during posterior ocular surgeries both during and after the surgical procedures. Further, cataract formation or acceleration can occur after intraocular surgery, especially following vitrectomy, a surgical technique for removing the vitreous used in the treatment of disorders that affect the posterior segment of the eye. This is associated with an accumulation of oxidants in the eye due to loss of the oxidant scavenging function of the natural vitreous.

Vitreoretinal surgery is employed in the later stages of diabetic retinopathy where vitrectomy and vitreous substitution are used in addition to laser treatment, and may be of use in the treatment of ARMD. In the treatment of rhegmatogenous retinal detachment, except for large tears, pneumatic retinopexy or scleral buckling is performed with the purpose of sealing the tear. Tamponade agents such as balanced salt solutions or silicone oil may be used to keep the retina in place (Colthurst et al., 2000). Sodium hyaluronate, a component of the vitreous, was tried as a substitute without much success (Delinger et al., 1980). Silicone oil is hydrophobic and has many side effects like emulsification, cataract formation, keratopathy and optic nerve atrophy (Giovanni et al., 1998).

SUMMARY

In accordance with one aspect, the present technology relates to a vitreous substitute which in various embodiments is nanoparticulate, capable of gelling in-situ, has anti-oxidant properties and delivering ocular drugs and actives. In one embodiment, the present disclosure provides a vitreous substitute comprising α-tocopheryl polyethylene glycol succinate (TPGS) and a polymeric blend of gellan and polyvinyl alcohol (PVA). In some embodiments, the polymeric blend comprises PVA and gellan in a ratio of from about 2:1 (w/w) to about 8:1 (w/w). In certain embodiments, the polymeric blend comprises PVA and gellan in a ratio of about 4:1 (w/w). In some embodiments, the polymeric blend is present at a final concentration from about 3% to about 7% by weight. In some embodiments, the TPGS is present at a final concentration from about 1 to about 2 mg/mL.

In one embodiment, the vitreous substitute further comprises drug-loaded nanoparticles. In some embodiments, the drug-loaded nanoparticles are chitosan nanoparticles. In some embodiments, the chitosan nanoparticles contain from about 10 μg/mL to about 100 μg/mL of the drug. In some embodiments, the drug is selected from the group consisting of an antibiotic, an antioxidant, and an anti-vascularization agent. In some embodiments, the antibiotic is ciprofloxacin hydrochloride. In some embodiments, the anti-vascularization agent is an anti-VEGF antibody. In some embodiments, the chitosan nanoparticles are present at a concentration from about 0.1 mg/mL to about 1 mg/mL.

In another aspect, the present disclosure provides a method for at least partially replacing the vitreous of a subject, the method comprising: administering to the vitreous cavity of an eye of the subject an effective amount of a liquid vitreous substitute comprising a polymeric blend of gellan and polyvinyl alcohol (PVA); administering to the vitreous cavity of the eye of the subject an effective amount of a cross-linker, wherein the liquid vitreous substitute forms a gel in the vitreous cavity.

In some embodiments of the method, the cross-linker comprises divalent cations. In some embodiments, the cross-linker is a calcium chloride solution. In some embodiments, the vitreous substitute and the cross-linker are administered simultaneously via a dual syringe assembly. In other embodiments, the vitreous substitute and the cross-linker are administered sequentially in either order.

In yet another aspect, a method for making a liquid vitreous substitute is provided, the method comprising: heating gellan and water to a temperature from about 80° C. to about 90° C. to form a gellan solution; adding polyvinyl alcohol (PVA) to the gellan solution; cooling the solution to a temperature from about 35° to about 55° C.; adding α-tocopheryl polyethylene glycol succinate (TPGS) to the solution; stirring the solution until the TPGS is completely dissolved and a clear liquid vitreous substitute solution is obtained.

In some embodiments, the method further comprises adding a nanoparticle suspension to the solution after it has been cooled to a temperature from about 35° to about 55° C. In some embodiments, the PVA and gellan are added in a ratio of from about 2:1 (w/w) to about 8:1 (w/w). In some embodiments, the total amount of PVA and gellan in the solution is from about 3% to about 7% by weight.

In one aspect, a kit for making a liquid vitreous substitute is provided. In one embodiment, the kit comprises: α-tocopheryl polyethylene glycol succinate (TPGS), gellan, polyvinyl alcohol (PVA), and a cross-linker. In some embodiments, the cross-linker is calcium chloride.

The foregoing summary is illustrative only and is not intended to be in any way limiting. In addition to the illustrative aspects, embodiments, and features described above, further aspects, embodiments, and features will become apparent by reference to the following drawings and the detailed description.

DETAILED DESCRIPTION

Figure 1:
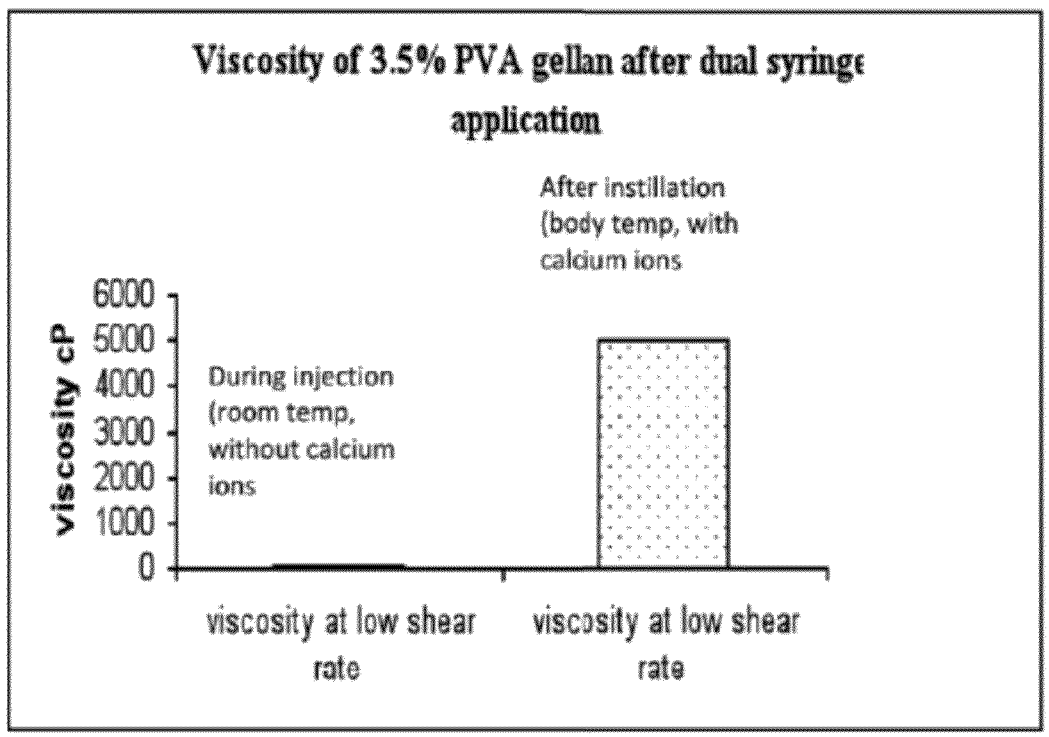
FIG. 1 is a chart showing an illustrative change in viscosity after in-situ gel formation with present vitreous substitute.

The present technology provides a nanoparticulate gelling vitreous substitute, which is a liquid at room temperature to aid easy administration, such as e.g. through a small needle incision, and forms a gel within the eye, which is hydrophilic in nature, similar to the natural vitreous. The biodegradable nanoparticles within the gel allow simultaneous loading of hydrophilic drugs or actives for sustained release in the posterior segment of the eye. The present vitreous substitute also has antioxidant properties which can reduce the oxidative stress on the lens which commonly occurs post-vitrectomy leading to cataracts. The vitreous substitute formulation comprises of a water-soluble natural or synthetic polymer and a gelling-agent which are blended together in the presence of a cross linker, to form a gel comprising of properties of the vitreous humor. The process of cross linking and gelation may occur in-situ. This can be achieved by dispensing to the eye, different components of the vitreous substitute in liquid state, along with the cross linking agent. Hence, the nature of the material is liquid in nature in-vitro and of a gel consistency in-vivo. The vitreous substitute may also an antioxidant and nanoparticles which are loaded with the required ocular drugs and actives for delivery in the posterior segment of the eye.

Thus, the present technology relates generally to vitreous substitutes, methods of forming the vitreous substitutes, kits for making vitreous substitutes and methods of using the substitutes as ocular delivery devices to treat a variety of eye disorders In the description that follows, a number of terms are used extensively. The terms described below are more fully understood by reference to the specification as a whole. Units, prefixes, and symbols may be denoted in their accepted SI form.

The terms "a" and "an" as used herein mean "one or more" unless the singular is expressly specified. Thus, for example, reference to a "drug" includes a mixture of two or more such compounds, as well as a single compound; reference to "an anti-vascularization agent" includes one or more anti-vascularization agents, and the like.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the "administration" of an agent, drag, or peptide to a subject includes any route of introducing or delivering to a subject a compound to perform its intended function. Administration can be carried out by any suitable route, including intraocularly, orally, intranasally, parenterally (intravenously, intramuscularly, intraperitoneally, or subcutaneously), or topically. Administration includes self-administration and the administration by another.

As used herein, the term "effective amount" refers to a quantity sufficient to achieve a desired therapeutic and/or prophylactic effect, e.g. an amount which results in the prevention of, or a decrease in, the symptoms associated with an ophthalmic condition. The amount of a composition administered to the subject will depend on the type and severity of the disease and on the characteristics of the individual, such as general health, age, sex, body weight and tolerance to drugs.

It will also depend on the degree, severity and type of disease. The skilled artisan will be able to determine appropriate dosages depending on these and other factors. The compositions can also be administered in combination with one or more additional therapeutic compounds. In the methods described herein, the vitreous substitute may be administered to a subject having one or more signs or symptoms of an ophthalmic condition. For example, a "therapeutically effective amount" of the ocular drug is meant at levels in which the physiological effects of an ophthalmic condition are, at a minimum, ameliorated.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for an ophthalmic condition if, after receiving a therapeutic amount of the ocular drugs or actives or agents according to the methods described herein, the subject shows observable and/or measurable reduction in or absence of one or more signs and symptoms of an ophthalmic condition. It is also to be appreciated that the various modes of treatment or prevention of medical conditions as described are intended to mean "substantial", which includes total but also less than total treatment or prevention, and wherein some biologically or medically relevant result is achieved.

As used herein, "prevention" or "preventing" of a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The tenors "eye," "globe," and "ocular tissue" are used to describe the sight organ in any organism. The term "ocular" refers to the eye, including all its muscles, nerves, blood vessels, tear ducts, membranes, etc., as well as structures that are immediately connected with the eye and its physiological functions. The terms "ocular," "ocular structures," and "eye" are used interchangeably throughout this disclosure. The term "vitroretinal" refers to the area comprised of retina and the vitreous humor.

The terms "back of the eye," "posterior portion of the globe," "posterior compartment," and "posterior retina" are used interchangeably and typically refer to any structure on the inner portion of the sclera that is posterior to the aqueous humor. These terms, for example, refer to the optic head, optic nerve, retina, choroid, circulatory vasculatures, lens, ciliary body, and ciliary process.

The term "anti-vascularization agent" refers to any compound capable of halting or decreasing the excessive growth of a vascular vessel by any variety of pharmacological mechanisms. The term "anti-vascularization agent" also includes a mixture or mixtures of different anti-vascularization agents with similar or varying mechanisms of action. For example, the anti-vascularization agent may work by inhibiting vascular endothelial growth factor (VEGF) and can, therefore, be used for antivascularization purposes.

The term "transport." as in the "transport" of a compound of interest across a body tissue, refers to passage of the compound in the direction of external to internal movement.

The terms "controlled release" or "sustained release" refers to the release of a given chug from a device at a predetermined rate. Such rate of release can be zero order, pseudo-zero order, first order, pseudo-first order and the like. Thus, relatively constant or predictably varying amounts of the drug can be delivered over a specified period of time The terms "drug," "compound," "active agent," "actives," "pharmaceutical composition," "pharmaceutical formulation," and "pharmacologically active agent" are used interchangeably herein to refer to any chemical compound, complex or composition, charged or uncharged, that is suitable for ocular administration and that has a beneficial biological effect, suitably a therapeutic effect in the treatment of a disease or abnormal physiological condition, although the effect may also be prophylactic in nature. The terms also encompass pharmaceutically acceptable, pharmacologically active derivatives of those active agents specifically mentioned herein, including, but not limited to, salts, esters, amides, prodrugs, active metabolites, analogs, and the like. When the terms "active agent," "pharmacologically active agent," and "drug" are used, then, or when a particular active agent is specifically identified, it is to be understood that applicants intend to include the active agent per se as well as pharmaceutically acceptable, pharmacologically active salts, esters, amides, prodrugs, conjugates, metabolites, analogs, etc.

The terms "disease," "oculopathy," "posterior ocular condition." "vitreoretinal disease" and "ocular pathology" refer to conditions that lead to pain or discomfort to the patient or in some way compromise or jeopardize visual acuity or site for the patient.

The terms "optional" and "optionally" mean that the subsequently described circumstance may or may not occur, so that the description includes instances where the circumstance occurs and instances where it does not.

Vitreous Substitutes

Disclosed herein are vitreous substitutes, methods of forming the vitreous substitutes, kits for making vitreous substitutes and methods of using the substitutes as ocular delivery devices to treat a variety of eye disorders Presently, there are no stable in-situ gelling hydrophilic materials available for vitreous replacement. The currently available vitreous substitutes are in the form of silicone oil and its derivatives which are high viscosity hydrophobic oils with low support to the retina and high toxicity due to irreversible cellular damage because of emulsification of oil droplets. Silicone oil leads to a keratopathy if it comes in contact with the cornea. Emulsified silicone oil tends to block the outflow of fluid from the eye and can lead to glaucoma. Silicone oil leads to damage of the myelin of the optic nerve and silicone oil droplets are stored as vacuoles in the optic nerve and lead to optic nerve atrophy. Hence, the currently available vitreous substitutes have high toxicity which can lead to blindness and necessitate their removal. They lead to increased incidence of cataract formation which leads to removal of the agent after a short term. The hydrophobic nature also prevents adequate coating of the vitreoretinal surfaces. Further, none of the currently available vitreous substitutes have antioxidant functions nor do they deliver any actives in the posterior segment of the eye. The present vitreous substitute would be a significant improvement as its benefits may include, but are not limited to, one or more of the following: 1) is hydrophilic and can coat ocular surfaces well; 2) forms the gel in-situ such that it can be easily administered in liquid state through a small incision; 3) is non-toxic; 4) acts as an oxidant scavenger; and 5) acts as a delivery agent for actives in the posterior segment of the eye.

In accordance with one aspect, the present technology relates to a vitreous substitute or replacement which is capable of gelling in-situ. Examples of substances which can be used as vitreous substitutes include any water-soluble polymers and/or gelling agents which can be crosslinked in-situ and form insoluble hydragel networks which act as vitreous substitutes. The water-soluble polymer can be a naturally occurring or a synthetic polymer or combinations thereof. Representative polymer substances which can be used include polyvinyl alcohol (PVA), hyaluronic acid (HA), polyvinyl pyrrolidinone (PVP), polyglyceryl methacrylate (PGMA), and combinations thereof. In an illustrative embodiment, the polymer substance is PVA. Suitable gelling agents include gellan gum xanthan gum, guar gum, locust bean gum, sodium carboxymethylcellulose, sodium alginate, agar, gelatin, carrageenan and combinations thereof. In an illustrative embodiment, the gelling agent is gellan. The polymer substance and the gelling agents are blended together to form a polymeric blend. These polymeric blends when contacted with a suitable cross-linking agent, at a suitable temperature, undergo crosslinking and gelation and form a gel which mimics the natural vitreous humor. Polymeric blends used as vitreous substitutes as disclosed herein are liquid at room temperature to aid administration to the ocular region and undergo crosslinking and gelation in-situ to form a gel comprising properties of vitreous humor. The polymeric blend in liquid state along with a suitable crosslinking agent can delivered to the ocular region.

Suitable crosslinking agents which can be used include any suitable ionic or covalent crosslinking agent which are mono- or poly-functional compounds having one or more functional groups which can react with one or more functional groups present in the polymer. In illustrative embodiments, crosslinking agents contain one or more of carboxyl, hydroxy, or amino functional groups. Where the polymer of the polymeric blend is cationically crosslinkable, the ionic crosslinker may contain ions selected from barium, calcium, magnesium, strontium, boron, beryllium, aluminum, iron, copper, and silver ions. Where the polymer of the polymeric blend is anionically crosslinkable, the ionic crosslinker may contain ions selected from phosphate, citrate, borate, succinate, maleate, adipate, and oxalate ions. In some embodiments, the polymeric blends are cross-linked by the addition of multivalent cations, such as divalent or trivalent metal cations in the form of salts, such as e.g., calcium chloride, zinc chloride, sodium chloride, aluminium chloride, copper sulfate, zinc acetate, etc. In an illustrative embodiment, the crosslinking agent is calcium chloride.

In some embodiments, the vitreous substitute may comprise an antioxidant in addition to the abovementioned polymeric blend. For example, antioxidants which can be used include Vitamin E, carotenoids, bioflavinoids, ascorbic acid and selenium, such as e.g., α-tocopheryl succinate, α-tocopheryl polyethylene glycol succinate, α-tocopheryl acetate, lutein, zeaxanthin, etc. In an illustrative embodiment, α-tocopheryl polyethylene glycol succinate is used as an antioxidant in the vitreous substitute.

In one aspect, the present disclosure provides a vitreous substitute comprising α-tocopheryl polyethylene glycol succinate (TPGS) and a polymeric blend of gellan and polyvinyl alcohol (PVA). The ratio of PVA and gellan in the polymeric blend and the concentration of polymeric blend in the vitreous composition can be adjusted depending upon the desired viscosity, wettability and gelation of the final vitreous substitute. In some embodiments, the ratio of PVA an gellan ranges from about 1:15 (w/w) to about 15:1 (w/w). In some embodiments, the ratio of PVA and gellan ranges from about 1:1 (w/w) to about 10:1 (w/w). In some embodiments, the polymeric blend comprises PVA and gellan in a ratio of from about 2:1 (w/w) to about 8:1 (w/w). In certain embodiments, the polymeric blend comprises PVA and gellan in a ratio of about 8:2 (w/w). In an illustrative embodiment, the polymeric blend comprises PVA and gellan in a ratio of about 4:1 (w/w). In some embodiments, the polymeric blend is present at a final concentration from about 0.5% to about 50% by weight. In some embodiments, the polymeric blend is present at a final concentration from about 1% to about 10% by weight. In some embodiments, the polymeric blend is present at a final concentration from about 3% to about 7% by weight.

Antioxidants present in the vitreous substitute are effective against several ocular diseases such as age-related macular degeneration (AMD), glaucoma, cataracts, ocular melanogenesis, etc. These antioxidants are, therefore, added to the vitreous substitute in suitable concentrations so as to be effective against such ocular diseases. Concentrations of antioxidants are described herein as an amount of the given antioxidant per milliliter of the composition as a whole. In one embodiment, the vitreous composition comprises TPGS, which imparts antioxidant properties to the vitreous substitute, at a concentration from about 0.01 mg/mL to about 5.0 mg/mL. In some embodiments, the TPGS is present at a final concentration from about 0.1 mg/mL to about 3.5 mg/mL. In an illustrative embodiment, the TPGS is present at a final concentration from about 1 mg/mL to about 2 mg/mL.

In some embodiments, the vitreous substitute is capable of delivering ocular drugs or actives. In one embodiment, the vitreous substitute further comprises drug-loaded nanoparticles. Any type of nanoparticles known in the art which are capable of association and delivery of bioactive macromolecules and compatible with the vitreous substituent can be used. In some embodiments, the nanoparticles are comprised of biocompatible and biodegradable hydrophilic polymers such as chitosan, polyethylene oxide, alginate, polyacrylate, methyl methacrylate, salts thereof, polycaprolactone, albumin, gelatin, solid lipid nanoparticles, derivatives thereof and combinations thereof. In some embodiments, the drug-loaded nanoparticles are chitosan nanoparticles. The concentration of nanoparticles in the composition depends on their size and the amount of drug to be delivered. In some embodiments, the chitosan nanoparticles are present at a concentration from about 0.001 mg/mL to about 10 mg/mL. In some embodiments, the chitosan nanoparticles are present at a concentration from about 0.01 mg/mL to about 3.0 mg/mL. In an illustrative embodiment, the chitosan nanoparticles are present at a concentration from about 0.1 mg/mL to about 1 mg/mL.

Any suitable drug for the treatment of an ocular disease may be loaded onto the nanoparticles. Suitable type of drugs which can be used include anesthetics, analgesics, anti-infectives, ocular hypotensive drugs, anti-inflamatory drugs, anti-bacterials, antioxidants, anticancer drugs, anti-vascularization drugs, drugs for dry eye and other ocular surface diseases, drugs for retinal diseases, dyes, nutritional agents, etc, or combinations thereof. In some embodiments, the drugs are hydrophilic in nature. In some embodiments, the drug is selected from the group consisting of: an antibiotic, an anti-oxidant, and an anti-vascularization agent. For example, antibiotics which can be used include chloramphenicol, sulphacetamide, oxytetracyline, polymyxin B, and fluoroquinolone antibiotics such as ciprofloxacin, lomefloxacin, norfloxacin, enoxacin, ofloxacin etc. In an illustrative embodiment, the antibiotic is ciprofloxacin hydrochloride. In some embodiments, the anti-vascularization agent is an anti-VEGF antibody. Other agents such as angiozyme, 2methoxyestradiol or thalidomide may also be used. Depending on the type of drug used, the appropriate quantity of drug can be loaded onto the nanoparticles. In some embodiments, the nanoparticles contain from about 0.1 μg/mL to about 10 mg/mL of the drug. In some embodiments, the nanoparticles contain from about 1 μg/mL to about 1 mg/mL of the drug. In some embodiments, the nanoparticles contain from about 10 μg/mL to about 100

μg/mL of the drug. In some embodiments, the nanoparticles are chitosan nanoparticles and contain from about 10 μg/mL to about 100 μg/mL of the drug.

Methods of Forming Vitreous Substitutes

In another aspect, a method for making a liquid vitreous substitute is provided. In some embodiments, the method comprises dissolving gellan or its derivative in a suitable solvent by heating it to a suitable temperature, adding polyvinyl alcohol to the gellan solution, cooling the solution, and adding an antioxidant to the solution to obtain a clear liquid vitreous substitute solution.

In one embodiment, a method for making a liquid vitreous substitute is provided, the method comprising: heating gellan and water to a temperature from about 80° C. to about 90° C. to form a gellan solution; adding polyvinyl alcohol (PVA) to the gellan solution; cooling the solution to a temperature from about 35° to about 55° C.; adding α-tocopheryl polyethylene glycol succinate (TPGS) to the solution; and stirring the solution until the TPGS is completely dissolved and a clear liquid vitreous substitute solution is obtained.

In some embodiments, the method further comprises adding a nanoparticle suspension to the solution after it has been cooled to a temperature from about 35° to about 55° C. In some embodiments, the nanoparticle suspension comprises chitosan nanoparticles and an ocular drug. In some embodiments, the ocular drug is selected from the group consisting of an antibiotic, an antioxidant, and an anti-vascularization agent. For example, antibiotics which can be used include chloramphenicol, sulphacetamide, oxytetracyline, polymyxin B, and fluoroquinolone antibiotics such as ciprofloxacin, lomefloxacin, norfloxacin, enoxacin, ofloxacin, etc. In an illustrative embodiment, the antibiotic is ciprofloxacin hydrochloride. In some embodiments, the anti-vascularization agent is an anti-VEGF antibody In some embodiments, the ratio of PVA an gellan ranges from about 1:15 (w/w) to about 15:1 (w/w). In some embodiments, the ratio of PVA and gellan ranges from about 1:1 (w/w) to about 10:1 (w/w). In some embodiments, the polymeric blend comprises PVA and gellan in a ratio of from about 2:1 (w/w) to about 8:1 (w/w). In certain embodiments, the polymeric blend comprises PVA and gellan in a ratio of about 8:2 (w/w). In an illustrative embodiment, the polymeric blend comprises PVA and gellan in a ratio of about 4:1 (w/w). In some embodiments, the polymeric blend is present at a final concentration from about 0.5% to about 50% by weight. In some embodiments, the polymeric blend is present at a final concentration from about 1% to about 10% by weight. In some embodiments, the polymeric blend is present at a final concentration from about 3% to about 7% by weight.

In one aspect, a kit for making a liquid vitreous substitute is provided. In one embodiment, the kit comprises α-tocopheryl polyethylene glycol succinate (TPGS), gellan, polyvinyl alcohol (PVA), and a cross-linker. In some embodiments, the cross-linker is calcium chloride.

Methods of Using Vitreous Substitutes

The vitreous substitute described herein can be use to partially or completely substitute or replace the natural or damaged vitreous of a subject. Thus in another aspect, the present disclosure provides a method for at least partially replacing the vitreous of a subject, the method comprising: administering to the vitreous cavity of an eye of the subject an effective amount of a liquid vitreous substitute comprising a polymeric blend of gellan and polyvinyl alcohol (PVA); administering to the vitreous cavity of the eye of the subject an effective amount of a cross-linker, wherein the liquid vitreous substitute forms a gel in the vitreous cavity. The homogeneous synthetic polymeric hydrogels thus formed are capable of mimicking the viscoelasticity and transparency of the natural vitreous humor.

The subjects include any animal that can benefit from the administration of the disclosed devices. In some embodiments, the subject is a mammal (e.g., a human, a rabbit, a primate, a dog, a cat, a horse, a cow, a pig, a rat, or a mouse). In some such embodiments, the subject is a human.

Suitable crosslinking agents such as those described above can be employed in the present methods. In some embodiments of the method, the cross-linker comprises divalent cations. In some embodiments, the cross-linker is a calcium chloride solution. The vitreous substitute and the cross-linker may be administered simultaneously or sequentially in any order. Suitable devices and methods can be employed to deliver the vitreous substitute and the cross-linker separately. For example, a dual syringe or tube delivery assembly containing the components of the hydrogel in separate chambers can be used. An illustrative embodiment of a dual syringe delivery assembly contains two syringes connected by a needle. The first syringe contains the vitreous substitute solution and the second syringe contains a crosslinking agent. Thus, in an illustrative embodiment, the vitreous substitute and the cross-linker are administered simultaneously via a dual syringe assembly. In other embodiments, the vitreous substitute and the cross-linker are administered sequentially in either order.

Therapeutic Methods

The present technology targets the entire sector of vitreoretinal or ocular diseases. The vitreous substitute can be used to treat a large spectrum of vitreoretinal or ocular diseases. These include age-related macular degeneration, vitreous degeneration, retinal tears, retinal detachment, diabetic retinopathy and traumatic, inflammatory and infective conditions affecting the posterior segment of the eye. Age-related degenerations of the vitreous or macula occur in about 70% of the population as part of the normal aging process. Retinal breaks occur in approximately 6% of the population, and retinal detachments in about 0.06%. The prevalence of low vision is 272 million worldwide. Macular degeneration has a prevalence of 32 million and cataracts have a prevalence of 54 million worldwide. Macular degeneration and other related vitreoretinal diseases cause a cumulative DALYs (disability adjusted life years) of 9 million. This technology addresses a large market of posterior segment eye diseases which are one of the leading and presently untreatable causes of blindness or low vision worldwide.

Another aspect of the technology includes methods of reducing an ophthalmic condition in a subject for therapeutic purposes. In therapeutic applications, compositions or medicaments are administered to a subject suspected of, or already suffering from, such a disease in an amount sufficient to cure, or at least partially arrest, the symptoms of the disease, including its complications and intermediate pathological phenotypes in development of the disease. As such, the disclosure provides methods of treating an individual afflicted with an ophthalmic condition.

The disclosed vitreous substitutes may be used to deliver various ocular drugs and treat a variety of eye disorders or traumas, and a variety of subjects. Eye disorders may include infections caused by bacteria or viruses, surgical procedures, and eye diseases such as glaucoma, cataracts, ocular melanoma, retinitis pigmentosa, elevated intraocular pressure, photoreceptor degeneration, intraocular neovascularization, vitreoretinopathy, retinal degeneration, retinal ischemia, retinal neovascularization, retinal pigment epithelium disease, and trachoma. Eye disorders may also include post-surgical periods where healing and/or infections may be a concern. By way of example only, the eye disorder may include a corneal infection. The corneal infection may include viral or bacterial keratitis.

Pharmaceutical compositions are typically formulated to be compatible with their intended route of administration. Examples of routes of administration include parenteral (e.g., intravenous, intradermal, intraperitoneal or subcutaneous), oral, inhalation, transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, pH can be adjusted with acids or bases, such as hydrochloric acid or sodium hydroxide. The parenteral preparation can be enclosed in ampoules, disposable syringes or multiple dose vials made of glass or plastic. For convenience of the patient or treating physician, the dosing formulation can be provided in a kit containing all necessary equipment (e.g., vials of vitreous substitute, vials of cross-linker, vials of diluent, syringes and needles) for a treatment course (e.g., 7 days of treatment).

Pharmaceutical compositions suitable for injectable use can include sterile aqueous solutions (where water soluble) or dispersions and sterile powders for the extemporaneous preparation of sterile injectable solutions or dispersion. In all cases, a composition should be sterile and should be fluid to the extent that easy syringability exists. It should be stable under the conditions of manufacture and storage and must be preserved against the contaminating action of microorganisms such as bacteria and fungi.

The vitreous substitute compositions can include a carrier, which can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thiomerasol, and the like. Glutathione and other antioxidants can be included to prevent oxidation. In many cases, isotonic agents may be included, for example, sugars, polyalcohols such as mannitol, sorbitol, or sodium chloride in the composition. Prolonged absorption of the injectable compositions can be brought about by including in the composition an agent which delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, typical methods of preparation include vacuum drying and freeze drying which can yield a powder of the active ingredient plus any additional desired ingredient from a previously sterile-filtered solution thereof.

The vitreous substitutes can be tested on various animal and human models to evaluate their efficacy in treating various ocular or vitreoretinal conditions. Animals used to model human eye diseases include nice, rats, dogs, cats, rabbits, monkeys, pigs, and guinea pigs. Potential diseases that may be modeled include, but are not limited to, eye infections, inflammatory eye diseases, neoplastic disorders, retinitis pigmentosa, elevated intraocular pressure, photoreceptor degeneration, intraocular neovascularization, vitreoretinopathy, retinal degeneration, retinal ischemic, retinal neovascularization, retinal pigment epithelium disease, and trachoma.

The present invention, thus generally described, will be understood more readily by reference to the following examples, which are provided by way of illustration and are not intended to be limiting of the present invention.

EXAMPLES

Example 1

Preparation of Vitreous Substitute

A polymeric blend was prepared by dispersing the required quantity of gellan in water and then heating it to a temperature of 90° C. and adding polyvinyl alcohol (PVA) to obtain a blend of PVA gellan at a ratio of 8:2 w/w with a final concentration of 3.5 to 7%. The solution was cooled to temperature of 40° C. and alpha-tocopherol polyethylene glycol 1000 succinate (TPGS) was added at a concentration of 1-2 mg/mL. The mixture was stirred continuously until the TPGS was completely dissolved and a clear solution was obtained. Similarly chitosan nanoparticles were prepared and added to the polymeric blend at 40° C. to attain a final concentration of 0.2 mg/mL of nanoparticles containing 20 µg/mL of the drug. The nanoparticle suspension was added when the gel was cooled to a temperature of 40° C. Vigorous stirring ensured a uniform distribution of the nanoparticles. The chitosan nanoparticles are loaded with the desired hydrophilic drug like ciprofloxacin hydrochloride or other hydrophilic actives like antibiotics or antioxidants or anti-vascularisation agents like anti-VEGF which are required for treatment of infections of the vitreoretinal tissues, prevention of post vitrectomy cataracts and for treatment of age related macular degeneration respectively. The chitosan nanoparticles were prepared by ionic gelation using pentasodium tripolyphosphate as the anion. Calcium chloride solution was prepared at a concentration of 1 mM and was filled in one syringe of the dual syringe assembly while the polymeric blend was filled in the other syringe of the dual syringe assembly. The dual syringe applicator is used to extrude the contents of both the syringes such that cross linking to a gel like material is obtained in-situ after extrusion through the syringe.

Example 2

Characterization of the Vitreous Substitute

The vitreous substitute or replacement described above may be characterized using standard techniques known in the art and used to characterize natural vitreous humor. Thus, viscosity measurements for the vitreous substitute and individual components may be done using a viscometer at body temperature (37° C.). Viscosity is measured as a function of sheer rate or in some cases, as a function of temperature at a fixed sheer rate to study the transition from liquid to gel. Light transparency of the vitreous substitute indicates the clarity of vision and can be measured using a UV/VIS spectrophotometer. Distilled water is typically used as a blank and transparency is measured from 400-700 nm. The morphology of the vitreous substitute can be studied by taking electron micrographs, e.g., SEM, under different magnifications. Wettability of the vitreous substitute and its components can be calculated by measuring the contact angle. The materials can be coated on various glass slides and another liquid used as a standard (e.g., glycerol) is placed on each slide and the contact angle is measured. The results obtained for the above-mentioned tests and additional tests are used to characterize the vitreous substitute and are described below.

Viscosity. The vitreous substitute or replacement described herein is an in-situ gelling system. It is a liquid of low viscosity at room temperature on instillation and gels at 37° C. in the presence of calcium ions in the eye. It can be administered in a liquid state and will form a gel with increased viscosity inside the eye (FIG. 1). The figure shows that an illustrative vitreous substitute has a low viscosity on injection at room temperature, but forms a gel with a viscosity of 5000 cP at body temperature on mixing with a cross linker. Thus, the formulation acts as an in-situ gel.

Figure 2:
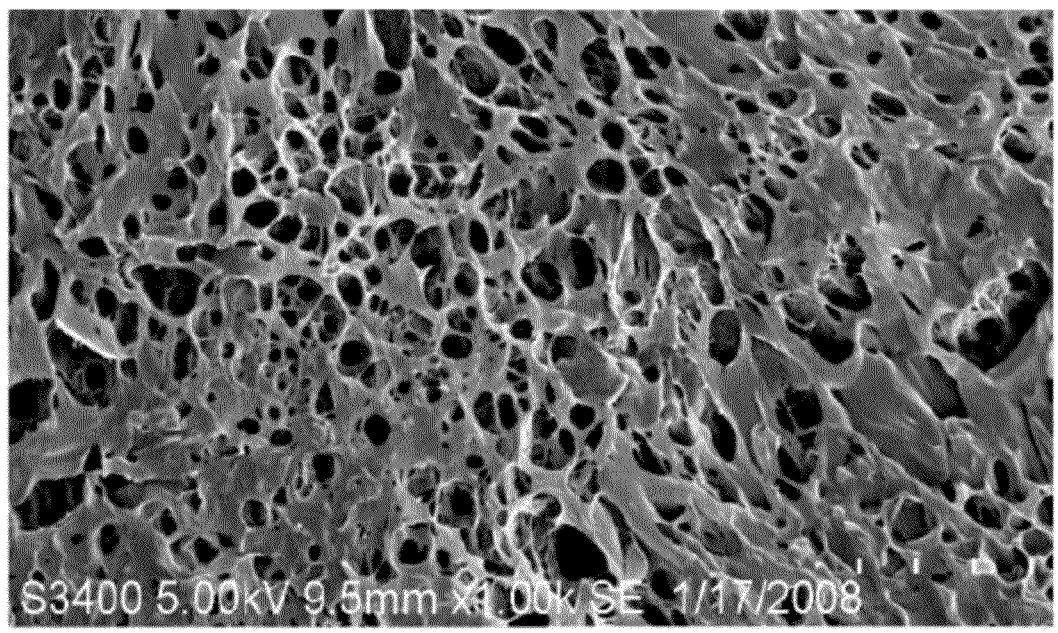
FIG. 2 shows scanning electron microscope image (SEM) of one illustrative formulation. A cross linked porous structure of the gel-like vitreous substitute is seen after in-situ cross linking with a cross linker at body temperature.

Morphology. Additionally, on cross linking with calcium ions, the vitreous substitute forms a meshwork gel which is porous in nature and can be characterized using scanning electron microscopy (FIG. 2).

Figure 3:
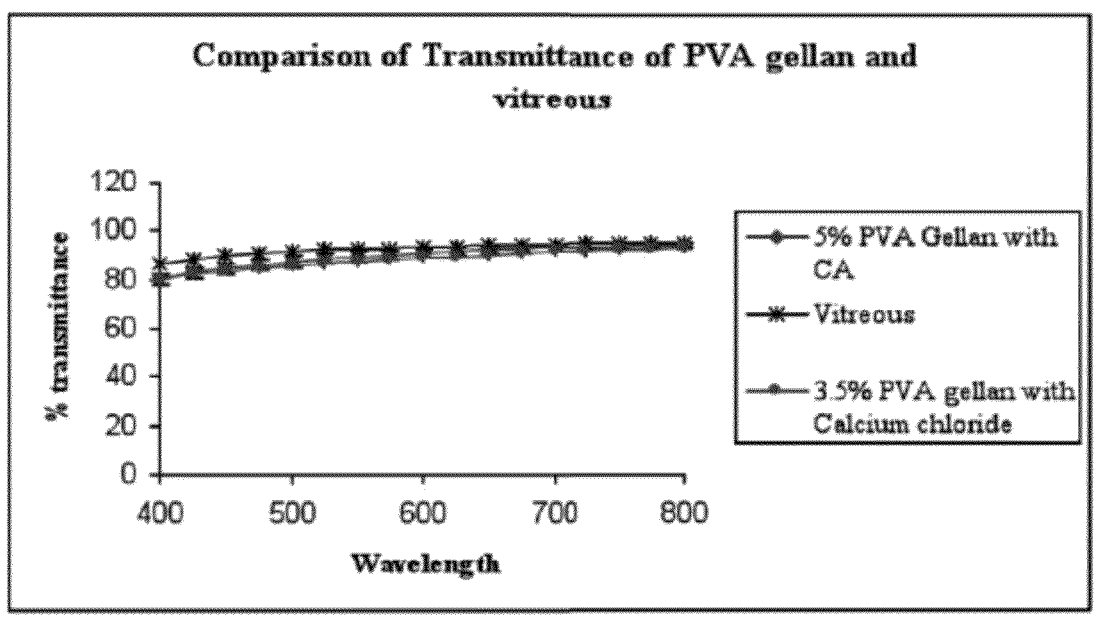
FIG. 3 shows light transmittance of an illustrative vitreous substitute with PVA, gellan and a cross-linker such as calcium chloride in comparison to the transmittance of the natural vitreous humor.
Figure 4:
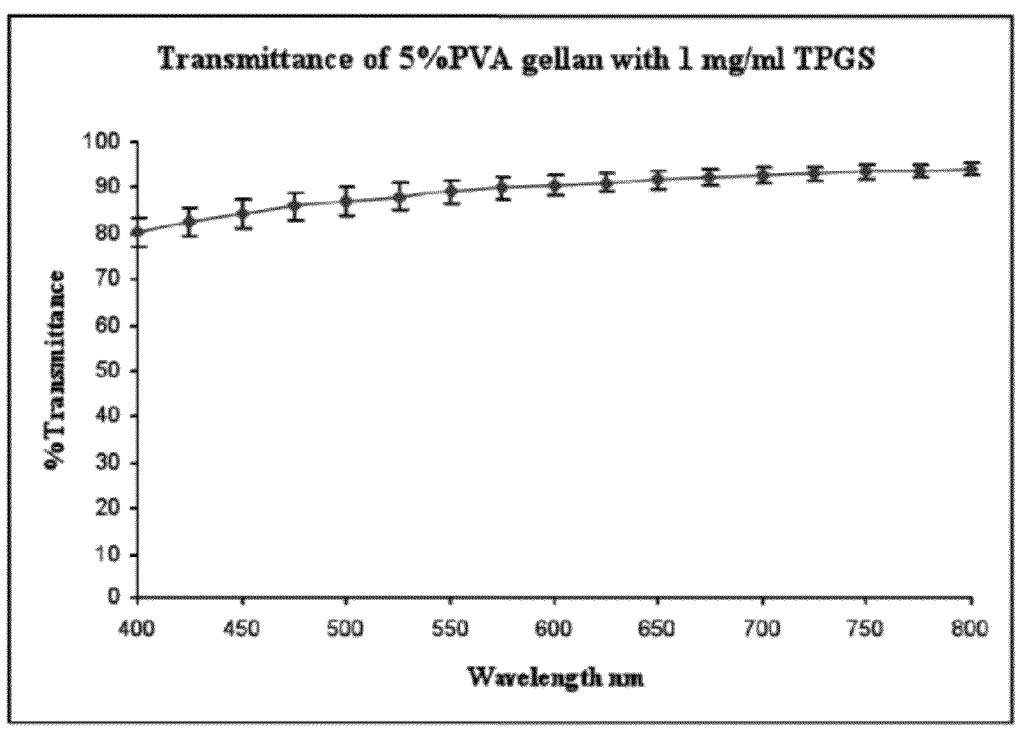
FIG. 4 shows light transmittance of an illustrative formulation in presence of TPGS.

Light transmittance. FIG. 3 and FIG. 4 depict charts for transmittance of the vitreous substitute and natural vitreous humor in the absence and presence of TPGS. It is observed that the vitreous substitute, both with and without TPGS, is transparent and has a high light transmittance (80-100%) which is comparable to the natural vitreous humor in the visible spectrum.

Figure 5:
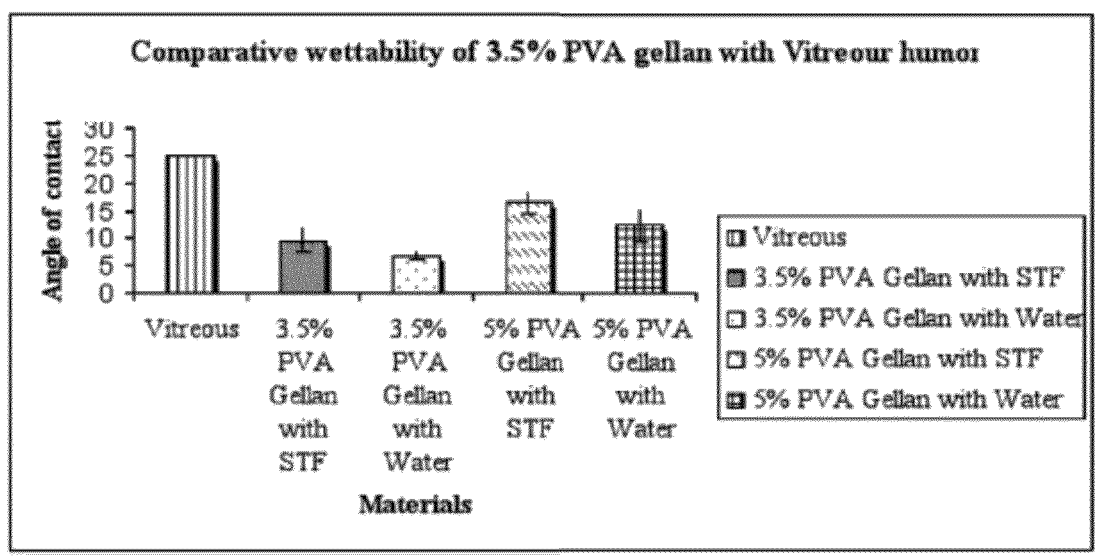
FIG. 5 shows contact angles of various illustrative compositions of vitreous substitute in comparison to the natural vitreous humor.
Figure 6:
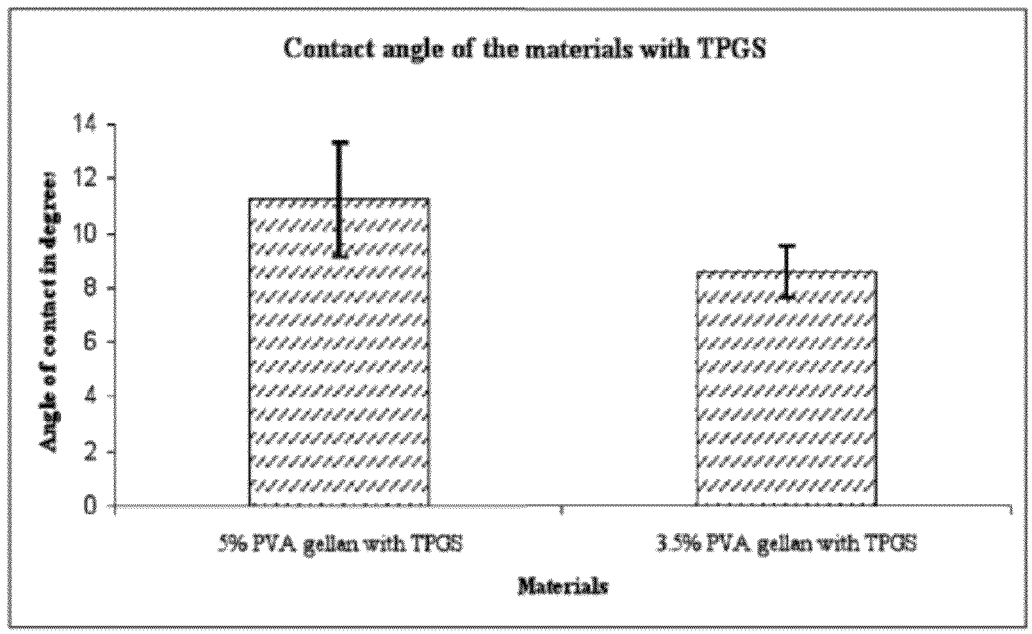
FIG. 6 shows contact angles of an illustrative vitreous substitute containing TPGS. The low water contact angle confirms the hydrophilic nature of the vitreous substitute.

Contact angle. Contact angle is an important measure of the wettability and adhesion properties of the vitreous substitutes. Natural vitreous humor is hydrophilic in nature and hence improved hydrophilic properties are desirable of the proposed vitreous replacements. The vitreous substitute of the present technology is hydrophilic in nature as is seen by the contact angles obtained with water (FIG. 5) and simulated tear fluid (STF) (FIG. 6) in ranges of 7 to 20 degrees. This is similar to the wettability of natural vitreous which is <20 degrees. In contrast, the water contact angle of silicone oil (one of the commonly used vitreous substitutes) is 55 degrees and its STF contact angle is 75 degrees, denoting its hydrophobic nature. This implies that the instant vitreous substitute will coat the vitreoretinal surfaces better and will not lead to emulsification droplets, which is a drawback of silicone oil and other commonly used vitreous replacements.

Figure 7:
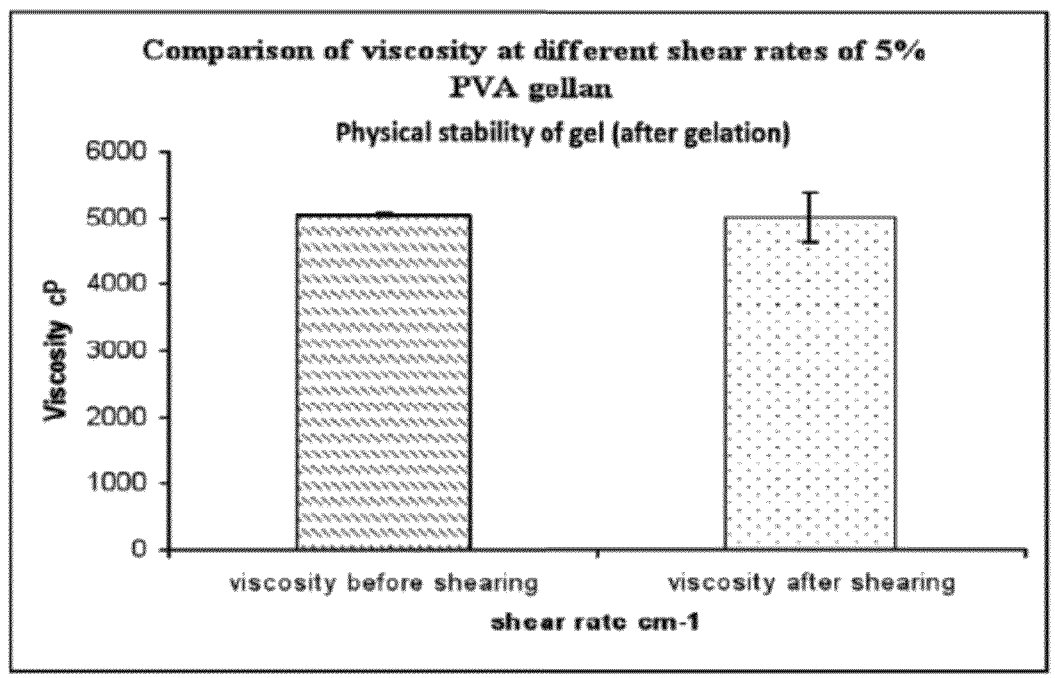
FIG. 7 shows viscosity of an illustrative vitreous substitute after gelation and on subjecting the gel to shears.
Figure 8:
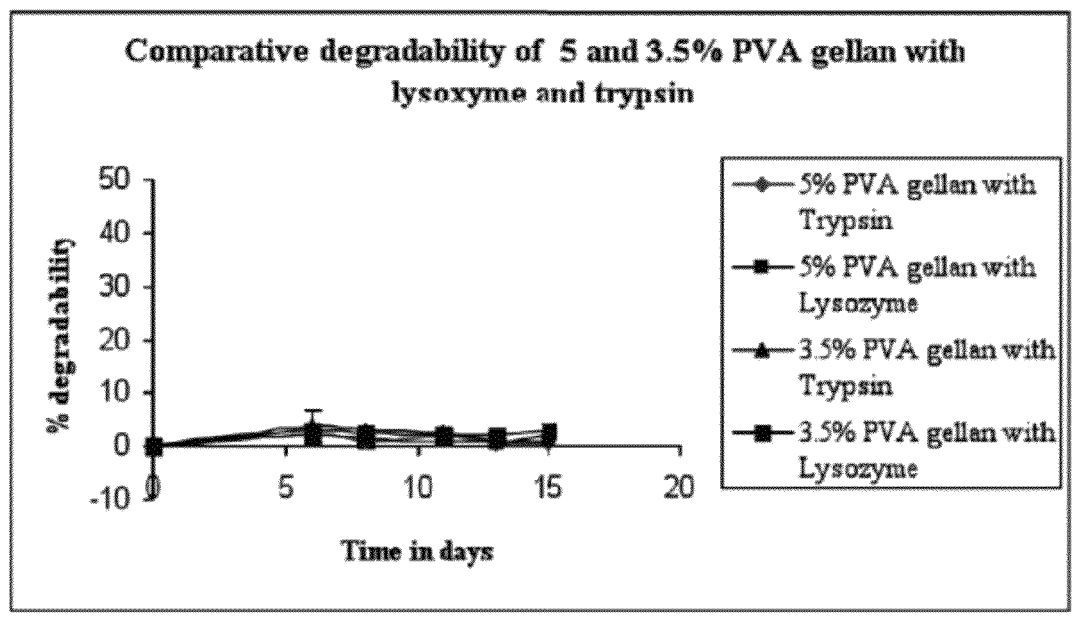
FIG. 8 shows in-vitro biochemical degradation of an illustrative formulation in presence of enzymes.

Shear stability. A comparison of the viscosity of vitreous substitute before and after shearing is depicted in FIG. 7. The chart shows that the vitreous substitute, after cross linking and gelation, maintains a high viscosity of 5000 cP even after shearing after gel formation. This indicates the physical stability of the gel. This has implications in maintaining an intact gel within the eye even when it is subjected to stress due to trauma or movement of the eyes and indicates the physical stability of the gel. Along with physical stability, the vitreous substitute also displays significant chemically stable and resists degradation in the presence of enzymes like lysozyme and trypsin, showing <2% degradation over a period of two weeks (FIG. 8).

Figure 9:
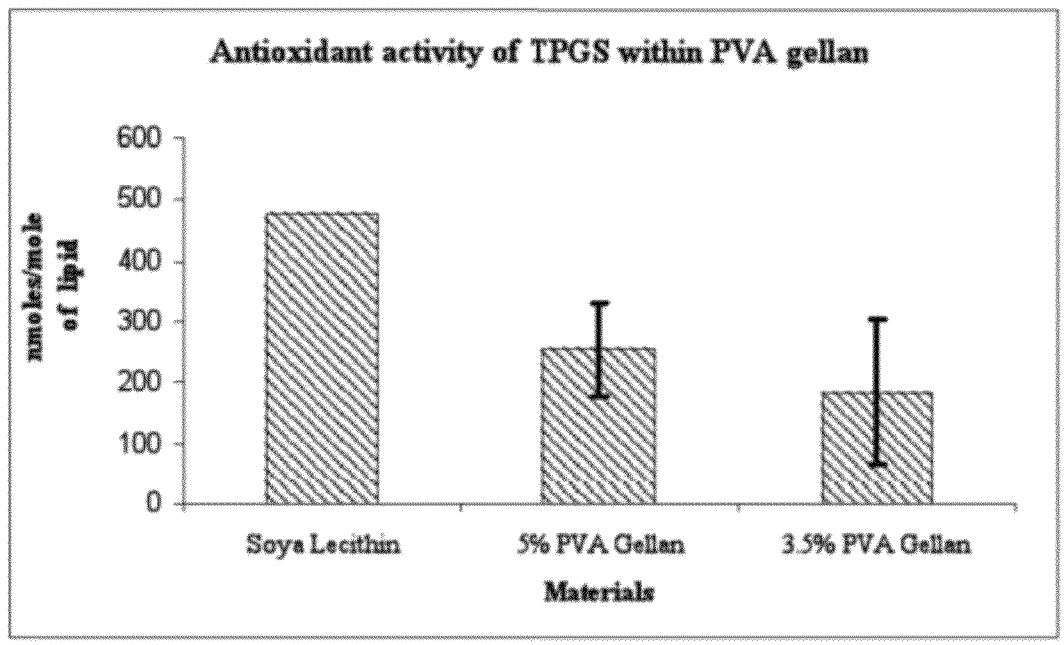
FIG. 9 shows the oxidant scavenger function an illustrative formulation. The amount of lipid peroxidation formed from soya lecithin, a model unsaturated phospholipid, in the absence and presence of the illustrative formulation is compared.

Anti-oxidant property. The vitreous substitute comprising PVA, gellan and TPGS demonstrated significant antioxidant activity. The amount of lipid peroxidation formed from soya lecithin, a model unsaturated phospholipid, in the absence and presence of the vitreous substitute is compared. A reduction in malondialdehyde formed is seen in the presence of the vitreous substitute indicating the antioxidant effect of the invented formulation. This can be seen from FIG. 9 which shows a marked reduction in the amount of malondialdehyde or lipid peroxidation products formed by soya lecithin in the presence of Fenton's reagent. The chart clearly shows the antioxidant effect of the vitreous substitute.

Irritancy index. When the instant vitreous substitute was administered to the eyes of the rabbits on the anterior surface of the cornea, the materials were found to be non toxic and showed a low ocular irritancy score as per Draize test (Table 1). The irritancy values obtained for the invented formulation by Draize test was zero, hence the invented formation was found to be nonirritant to the eye:

TABLE 1

| Irritancy Index | |
|---|---|
| Irritancy Index | Classification |
| 0-0.5 | Nonirritant |

Figure 10:
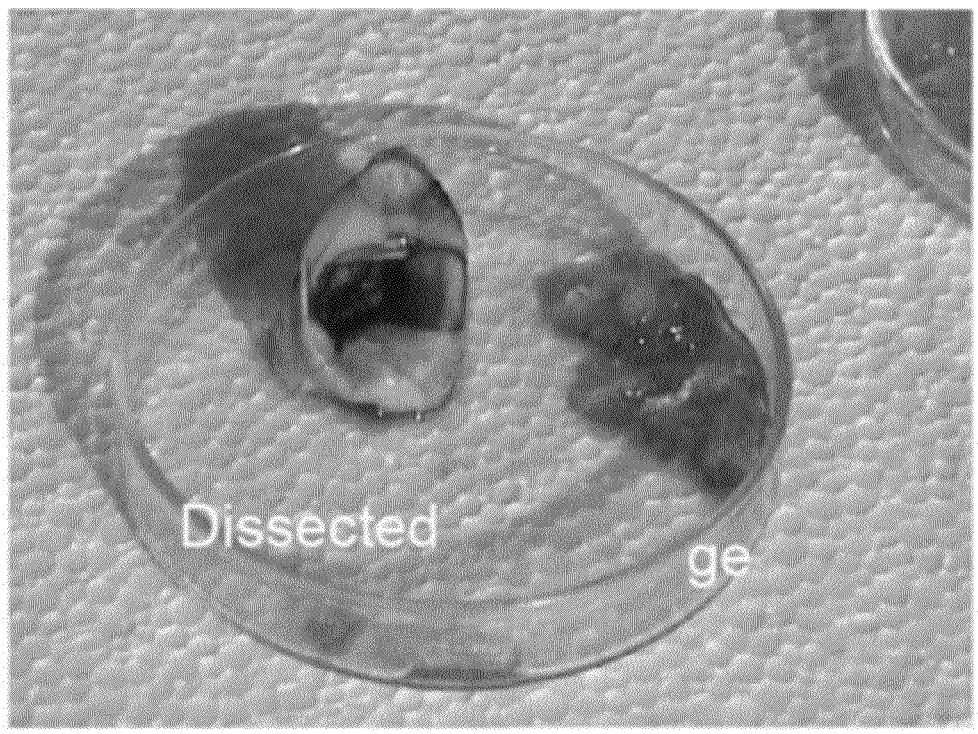
FIG. 10 shows the stability of the gel state of an illustrative vitreous substitute in the goat eyeball.

Gel stability. When the vitreous substitute was instilled in freshly excised goat eyeballs and incubated at 37° C. for 12 hours, gel formation takes place in-situ and the material remained in the gel state on dissection of the eyes after 12 hours (FIG. 10). This indicates the stability of the gel in simulated in-vivo conditions.

Figure 11:
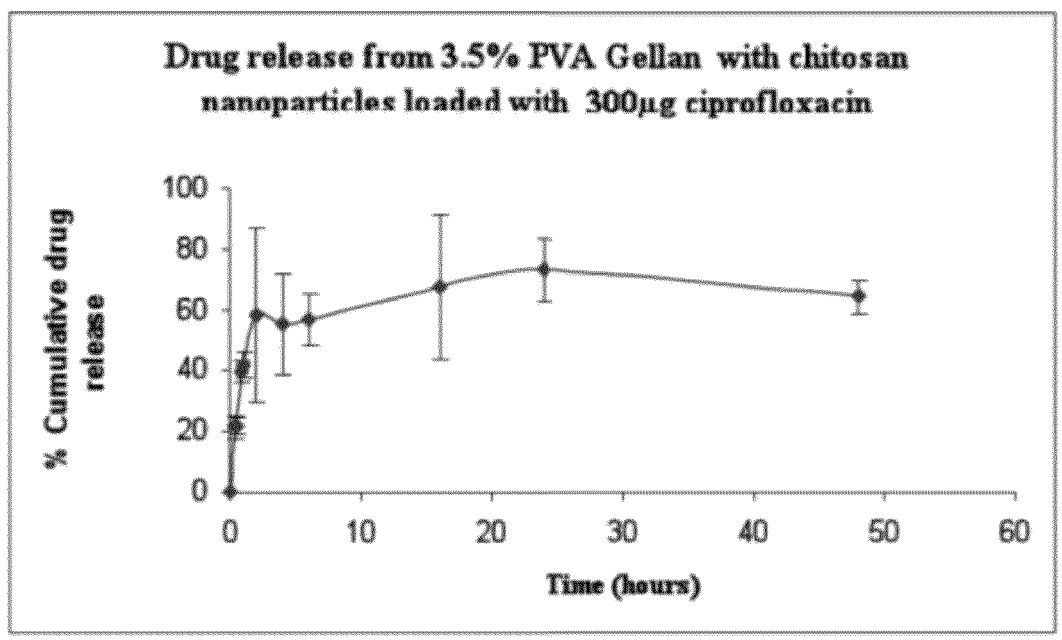
FIG. 11 shows drug release profile for an illustrative vitreous substitute comprising chitosan nanoparticles loaded ciprofloxacin hydrochloride.

Drug release profile. When loaded with 300 μg of ciprofloxacin hydrochloride, a hydrophilic drug, the invented formulation of nanoparticles within in-situ gel caused a slow sustained release of the drug over a period of 48-50 hours. The drug release profile is depicted in FIG. 11. This period can be further increased depending on the drug and the loading capacity.

Figure 12:
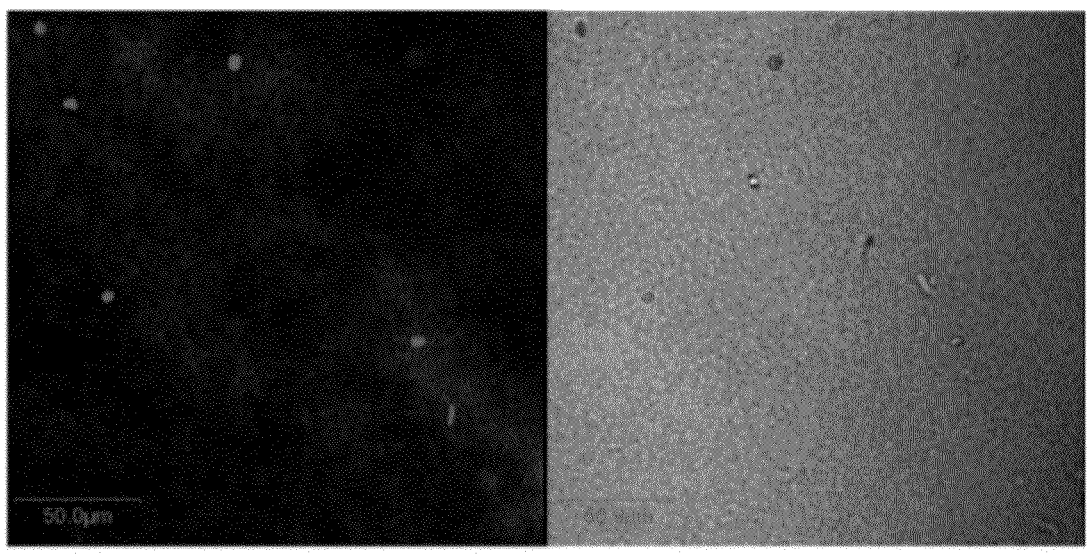
FIG. 12 is an image of the vitreoretinal tissue after incorporation of an illustrative dye loaded nanoparticulate vitreous substitute into rabbit eyes.

Dye penetration certificate. On in-vivo administration of the vitreous substitute containing dye loaded nanoparticles in in-situ gel, on the anterior surface of the rabbit eye, it penetrated into the posterior segment of the rabbit eye and showed fluorescence in the vitreoretinal tissues after 12 hours of administration, as seen in the image in FIG. 12. This suggests the feasibility of simultaneous release of actives from the invented vitreous substitute into the back of the eye as is required for treatment of vitreoretinal diseases.

EQUIVALENTS

While certain embodiments have been illustrated and described, it should be understood that changes and modifications can be made therein in accordance with ordinary skill in the art without departing from the technology in its broader aspects as defined in the following claims.

The embodiments, illustratively described herein, may suitably be practiced in the absence of any element or elements, limitation or limitations, not specifically disclosed herein. Thus, for example, the terms "comprising," "including," "containing," etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are untended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," and the like, include the number recited and refer to ranges which can be subsequently broken down into subranges as discussed above. Finally, as will be understood by one skilled in the art, a range includes each individual member.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A vitreous substitute comprising
α-tocopheryl polyethylene glycol succinate (TPGS) and a polymeric blend of gellan and polyvinyl alcohol (PVA).

2. The vitreous substitute of claim 1, wherein the polymeric blend comprises PVA and gellan in a ratio of from about 2:1 (w/w) to about 8:1 (w/w).

3. The vitreous substitute of claim 1, wherein the polymeric blend is present at a final concentration from about 3% to about 7% by weight.

4. The vitreous substitute of claim 1, wherein the TPGS is present at a final concentration from about 1 to about 2 mg/mL.

5. The vitreous substitute of claim 1 further comprising drug-loaded nanoparticles.

6. The vitreous substitute of claim 5, wherein the drug-loaded nanoparticles are chitosan nanoparticles.

7. The vitreous substitute of claim 6, wherein the chitosan nanoparticles contain from about 10 µg/mL to about 100 µg/mL of the drug.

8. The vitreous substitute of claim 5, wherein the drug is selected from the group consisting of an antibiotic, an antioxidant, and an anti-vascularization agent.

9. The vitreous substitute of claim 8, wherein the antibiotic is ciprofloxacin hydrochloride.

10. The vitreous substitute of claim 8, wherein the anti-vascularization agent is an anti-VEGF antibody.

11. The vitreous substitute of claim 6, wherein the chitosan nanoparticles are present at a concentration from about 0.1 mg/mL to about 1 mg/mL.

12. A method for at least partially replacing the vitreous of a subject, the method comprising:
   administering to the vitreous cavity of an eye of the subject an effective amount of the liquid vitreous substitute of claim 1; and
   administering to the vitreous cavity of the eye of the subject an effective amount of a cross-linker, wherein the liquid vitreous substitute forms a gel in the vitreous cavity.

13. The method of claim 12, wherein the cross-linker comprises divalent cations.

14. The method of claim 12, wherein the cross-linker is a calcium chloride solution.

15. A method for making a liquid vitreous substitute, the method comprising:
   heating gellan and water to a temperature of about 80° C. to about 90° C. to form a gellan solution;
   adding polyvinyl alcohol (PVA) to the gellan solution;
   cooling the solution to a temperature of about 35° to about 55° C.;
   adding α-tocopheryl polyethylene glycol succinate (TPGS) to the solution;
   stirring the solution until the TPGS is completely dissolved and a clear liquid vitreous substitute solution is obtained.

16. The method of claim 15 further comprising adding a nanoparticle suspension to the solution after it has been cooled to a temperature of about 35° to about 55° C.

17. The method of claim 15, wherein the PVA and gellan are added in a ratio of about 2:1 (w/w) to about 8:1 (w/w).

18. The method of claim 17, wherein the total amount of PVA and gellan in the solution is from about 3% to about 7% by weight.

19. A kit for making a liquid vitreous substitute, the kit comprising: α-tocopheryl polyethylene glycol succinate (TPGS), gellan, polyvinyl alcohol (PVA), and a cross-linker.

20. The kit of claim 19, wherein the cross-linker is calcium chloride.

* * * * *

UNITED STATES PATENT AND TRADEMARK OFFICE
CERTIFICATE OF CORRECTION

PATENT NO. : 8,343,471 B2
APPLICATION NO. : 13/140747
DATED : January 1, 2013
INVENTOR(S) : Banerjee et al.

It is certified that error appears in the above-identified patent and that said Letters Patent is hereby corrected as shown below:

On the Title Page, in Item (54), in Title, and in the Specification, Column 1, Lines 1-3, delete "NANOPARTICULATE IN-SITU GELS OF TPGS, GELLAN AND PVA AS VITREOUS HUMOR SUBSTITUTES" and insert -- NANOPARTICULATE IN-SITU GELS AS VITREOUS HUMOR SUBSTITUTES FOR OCULAR DISEASES --, therefor.

On the Title Page, in Item (56), under "OTHER PUBLICATIONS", in Column 2, Line 34, delete ""in" and insert -- "In --, therefor.

In the Specification:

In Column 1, Line 17, delete "vitroretinal" and insert -- vitreoretinal --, therefor.

In Column 4, Line 52, delete "drag," and insert -- drug, --, therefor.

In Column 5, Line 34, delete "tenors" and insert -- terms --, therefor.

In Column 5, Line 41, delete ""vitroretinal"" and insert -- "vitreoretinal" --, therefor.

In Column 5, Line 59, delete ""transport."" and insert -- "transport," --, therefor.

In Column 5, Line 63, delete "chug" and insert -- drug --, therefor.

In Column 6, Lines 20-21, delete "condition."" and insert -- condition," --, therefor.

In Column 6, Line 33, delete "disorders" and insert -- disorders. --, therefor.

In Column 7, Line 4, delete "pyrrolidinone" and insert -- pyrrolidone --, therefor.

In Column 7, Line 7, delete "gum" and insert -- gum (gellan), --, therefor.

Signed and Sealed this
Eighteenth Day of June, 2013

Teresa Stanek Rea
*Acting Director of the United States Patent and Trademark Office*

CERTIFICATE OF CORRECTION (continued)
U.S. Pat. No. 8,343,471 B2

In Column 7, Line 58, delete "an" and insert -- and --, therefor.

In Column 8, Line 46, delete "anti-inflamatory" and insert -- anti-inflammatory --, therefor.

In Column 9, Line 35, delete "antibody" and insert -- antibody. --, therefor.

In Column 9, Line 36, delete "an" and insert -- and --, therefor.

In Column 11, Line 36, delete "syringability" and insert -- syringeability --, therefor.

In Column 12, Line 7, delete "nice," and insert -- mice, --, therefor.

In Column 12, Line 13, delete "ischemic," and insert -- ischemia, --, therefor.

In Column 14, Lines 59-60, delete ""including."" and insert -- "including," --, therefor.

In Column 15, Line 14, delete "untended" and insert -- intended --, therefor.

In Column 15, Line 47, delete "language" and insert -- languages --, therefor.

In the Claims:

In Column 15, Line 61, in Claim 1, delete "comprising" and insert -- comprising: --, therefor.